United States Patent
Feenstra et al.

(10) Patent No.: US 6,911,448 B2
(45) Date of Patent: Jun. 28, 2005

(54) PIPERAZINE AND PIPERIDINE COMPOUNDS

(75) Inventors: Roelof W. Feenstra, Weesp (NL); Johannes A. M. van der Heijden, Weesp (NL); Cornelis G. Kruse, Weesp (NL); Stephen K. Long, Weesp (NL); Gustaaf J. M. van Scharrenburg, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 135 days.

(21) Appl. No.: 10/257,677

(22) PCT Filed: May 10, 2001

(86) PCT No.: PCT/EP01/05320

§ 371 (c)(1),
(2), (4) Date: Oct. 15, 2002

(87) PCT Pub. No.: WO01/85725

PCT Pub. Date: Nov. 15, 2001

(65) Prior Publication Data

US 2003/0119849 A1 Jun. 26, 2003

(30) Foreign Application Priority Data

May 12, 2000 (EP) .............................................. 00201699

(51) Int. Cl.$^7$ .................. A61K 31/496; A61K 31/4439; A61K 31/454; C07D 413/10; C07D 413/14
(52) U.S. Cl. .............................. 514/253.1; 514/254.02; 514/318; 514/321; 514/333; 514/338; 544/364; 544/368; 546/194; 546/198; 546/256; 546/270.1; 546/271.7
(58) Field of Search ................................ 544/364, 368; 546/194, 198, 256, 270.1, 271.7; 514/253.1, 254.02, 318, 321, 333, 338

(56) References Cited

U.S. PATENT DOCUMENTS 4,737,505 A 4/1988 Guillaume et al. ......... 514/323

FOREIGN PATENT DOCUMENTS

| EP | 0 169 148 A1 | 1/1986 |
|----|----|----|
| EP | 0 190 472 A1 | 6/1986 |
| EP | 0 189 612 A1 | 8/1986 |
| JP | 60-126275 | * 7/1985 |
| WO | WO 97/36893 | 10/1997 |
| WO | 01/85168 A1 | * 11/2001 |

OTHER PUBLICATIONS

English Translation for Michiaki et al, JP 60–126275 (Jul. 1985).*
Patent Abstract of Japan for JP 60–126275 (Jul. 1985).*
Robichaud et al. in Annualr Reports in Medicinal Chemistry, vol. 35, p. 11–20 (2000).*
TenBrink et al in Annual Reports in Medicinal Chemistry, vol. 29, p. 43–51 (1994).*
Perrone et al. J. Med. Chem. vol. 42, p. 490–496 (1999).*
Perrone et al. Bioorganic & Medicinal Chemistry vol. 8, p.873–881 (2000).*
International Search Report for PCT/EP 01/05320.

* cited by examiner

Primary Examiner—Emily Bernhardt
(74) Attorney, Agent, or Firm—Finnegan, Henderson, Farabow, Garrett & Dunner, L.L.P.

(57) ABSTRACT

The invention relates to a group of novel piperazine and piperidine derivatives of the formula wherein Y is hydrogen, halogen, alkyl (1–3C), or CN, $CF_3$, $OCF_3$, $SCF_3$, alkoxy (1–3C), amino or mono- or dialkyl(1–3C) substituted amino or hydroxy, X is O, S, SO or $SO_2$, ---Z represents —C, =C or —N, $R_1$ and $R_2$ independently represent hydrogen or alkyl (1–3C), Q is benzyl or 2-, 3- or 4-pyridylmethyl, wich groups may be substited with one or more more substituents from the group halogen, nitro, cyano, amino, mono- or di (1–3C)alkylamino, (1–3C) alkoxy, $CF_3$, $OCF_3$, $SCF_3$, (1–4C)-alkyl, (1–3C)alkylsulfonyl or hydroxy, and salts and prodrugs thereof. It has been found that these compounds have interesting pharmacological properties due to a combination of (partial) agonism towards the members of the dopamine $D_2$-receptor subfamily and affinity for relevant serotonin and/or noradrenergic receptors (I)

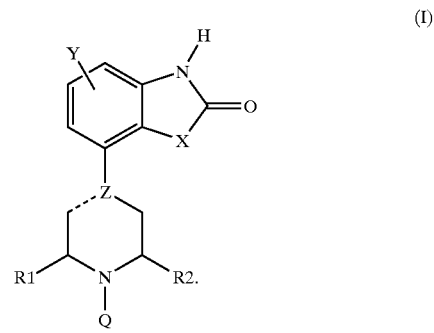

10 Claims, No Drawings

PIPERAZINE AND PIPERIDINE COMPOUNDS

The present invention relates to a new group of piperazine and piperidine derivatives having interesting pharmacological properties due to a combination of (partial) agonism towards the members of the dopamine $D_2$-receptor subfamily and affinity for relevant serotonin and/or noradrenergic receptors.

It is known from EP 0189612 that piperazine derivatives substituted at one nitrogen with a phenyl-heterocyclic group, and unsubstituted at the other nitrogen atom, have psychotropic activity.

Further it is known from EP 0190472 that benzofuran- and benzodioxole-piperazine derivatives substituted at the other nitrogen atom of the piperazine group, have also psychotropic activity. Finally it is known from EP 0169148 that 1,3-dihydro-4-(1-ethyl-1,2,3,6-tetrahydropyridin-4-yl)-2H-indol-2-one and similar compounds have analgetic properties.

It has now surprisingly been found that a small group of piperazine and piperidine derivatives having formula (I)

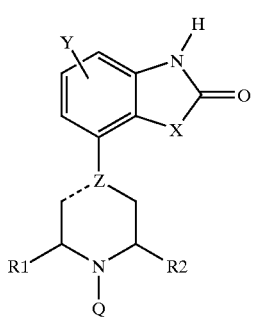

(I)

wherein

Y is hydrogen, halogen, alkyl (1–3C), or CN, $CF_3$, $OCF_3$, $SCF_3$, alkoxy(1–3C), amino or mono- or dialkyl(1–3C) substituted amino or hydroxy, X is O, S, SO or $SO_2$, ---Z represents —C, =C or —N, $R_1$ and $R_2$ independently represent hydrogen or alkyl (1–3C), Q is benzyl or 2-, 3- or 4-pyridylmethyl, wich groups may be substited with one or more substituents from the group halogen, nitro, cyano, amino, mono- or di (1–3C)alkylamino, (1–3C) alkoxy, $CF_3$, $OCF_3$, $SCF_3$, (1–4C)-alkyl, (1–3C)alkylsulfonyl or hydroxy, and salts and prodrugs thereof have a combination of (partial) dopamine $D_2$-receptor subfamily agonism and affinity for relevant serotonergic and/or noradrenergic receptors.

Preferred compounds according to the invention are compounds of the formula (I) wherein Y, $R_1$ and $R_2$ are hydrogen, X represents oxygen, and ---Z and Q have the above meanings, and the salts thereof.

Especially preferred are the compounds wherein Y, $R_1$ and $R_2$ are hydrogen, X is oxygen, ---Z represents —N and Q is optionally substituted benzyl.

Compounds according to the invention show affinities for at least two members of the dopamine $D_2$ receptor subfamily (pKi range 6.0–9.5) and a relevant serotonin (5-$HT_{1A}$, 5$HT_{5A}$, 5$HT_7$) receptor (pKi range 5.0–8.0) and/or noradrenergic ($\alpha_1$, $\alpha_2$) receptors, measured according to well-defined methods (e.g.: Creese I, Schneider R and Snyder S H, [$^3$H]-Spiroperidol labels dopamine receptors in rat pituitary and brain, *Eur J Pharmacol* 1997, 46: 377–381 and Gozlan H, E I Mestikawy S, Pichat L, Glowinsky J and Hamon M, 1983, Identification of presynaptic serotonin autoreceptors using a new ligand $^3$H-PAT, *Nature* 1983, 305:140–142).

The compounds show varying activities as (partial) agonists towards members of the dopamine $D_2$ receptor subfamily and surprisingly towards the serotonin 5-$HT_{1A}$ receptor and/or noradrenergic $\alpha_1$ receptor. This activity in general was measured on the formation of adenylate cyclase in cell-lines expressing these cloned receptors (e.g. human $D_2$ receptors and 5-$HT_{1A}$ receptors expressed in CHO cell line according to the methods described by Solomon Y, Landos C, Rodbell M, 1974, A highly selective adenylyl cyclase assay, *Anal Biochem* 1974, 58:541–548 and Weiss S, Sebben M and Bockaert J J, 1985, Corticotropin-peptide regulation of intracellular cyclic AMP production in cortical neurons in primary culture, *J Neurochem* 1985, 45:869–874).

The unique combination of (partial) dopamine $D_2$-receptor subfamily agonism and affinity towards relevant serotonin- and/or noradrenergic- receptors results in a surprisingly broad activity in several animal models, predictive for psychiatric and/or neurologic disturbances. The compounds show a surprisingly high efficacy in a therapeutic model for anxiolytic/antidepressant activity: the conditioned ultrasonic vocalization model in rats (see e.g.: Molewijk H E, Van der Poel A M, Mos J, Van der Heyden J A M and Olivier B (1995), Conditioned ultrasonic vocalizations in adult male rats as a paradigm for screening anti-panic drugs, *Psychopharmacology* 1995, 117: 32–40). The activity of the compounds in this model was in the low microgram/kg range, which is surprisingly more active (by a factor 100 to 3000) compared to the compounds previously described in EP 0190472 and EP 0398413.

In addition these compounds also show effects in models predictive for antidepressant activity at higher doses (forced swim test, see e.g.: Porsolt R D, Anton G, Blavet N and Jalfre M, 1978, Behavioural despair In rats: A new model sensitive to antidepressant treatments, *Eur J Pharmacol* 1978, 47:379–391 and the differential reinforcement of low rates of responding model in rats, see e.g.: McGuire P S and Seiden L S, The effects of tricyclic antidepressants on performance under a differential-reinforcement-of-low-rate schedule in rats, *J Pharmacol Exp Ther* 1980, 214: 635–641).

Depending on the degree of partial agonism towards the dopamine $D_2$-receptor subfamily, compounds tend to behave like full dopamine receptor agonists in induced climbing behaviour in mice, or, in the presence of a full dopamine receptor agonist, behave like a dopamine antagonist in the, e.g. apomorphine-induced climbing behaviour in mice (antagonism of apomorphine-induced climbing behaviour in mice, e.g.: Costall B, Naylor R J and Nohria V, Differential actions of typical and atypical agents on two behavioural effects of apomorphine in the mouse, *Brit J Pharmacol* 1978, 63: 381–382; suppression of locomotor activity, e.g.: File S E and Hyde J R G, A test of anxiety that distinguishes between the actions of benzodiazepines and those of other minor tranquillisers or stimulants, *Pharmacol Biochem Behav* 1979, 11: 65–79). Compounds of the invention show potent efficacy in animal models predictive of anti-Parkinsonian activity. These include 6-OH-DA induced turning behavior in rats (Ungerstedt U, 6-OH-DA induced degeneration of central monoamine neurons, *Eur. J. Pharmacol.* 1968 5: 107–110), MPTP-lesioned Marmoset monkey (Nomoto M, Jenner P, Marsden C D: The dopamine agonist $D_2$ agonist LY 141865 but not the $D_1$ agonist SKF 38393, reverses Parkinsonism induced by 1-methyl-4-phenyl-1,2,3,6-tetrahydropyridine (MPTP) in the common Marmoset. *Neurosci. Lett.*, (1985) 57: 37–41). Surprisingly, compounds of the invention lack the unwanted side effects associated with currently used dopaminergic drugs, including induction of stereotypy, nausea, dizziness and vomiting.

The compounds are of value in the treatment of affections or diseases of the central nervous system, caused by disturbances of the dopaminergic and/or serotonergic and/or noradrenergic systems, for example: addiction (including craving), anxiety disorders (including e.g. generalised anxiety, panic, obsessive compulsive disorder), depression, autism, schizophrenia, Parkinson's disease, disturbances of cognition and memory.

Suitable acids with which the compounds of the invention can form acceptable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methane sulphonic acid and naphtalene sulphonic acid.

Prodrugs are derivatives of the compounds having formula (I) wherein a group is present which is easily removed after administration. Suitable prodrugs for example are compounds containing one of the following groups: amidine, enamine, a Mannich base, a hydroxy-methylene derivative, an O-(acyloxymethylene carbamate) derivative, carbamate or enaminone.

The compounds and the salts thereof can be brought Into forms for administration by means of usual processes using auxiliary substances such as liquid and solid carrier materials.

The compounds of the invention can be prepared according to methods known for the synthesis of analogous compounds.

Method A

Compounds having formula (I) wherein ---Z represents —N or —C can be obtained by reacting the corresponding compound wherein Q is hydrogen with a compound Q-Hal, wherein Q has the above meanings and Hal is halogen, preferably bromine. This reaction can be carried out in a solvent such as acetonitrile in the presence of a base, for example ethyl-diisopropylamine or triethylamine.

The starting compounds wherein Q is hydrogen and ---Z is —N are known or can be obtained as described in EP 0189612. Starting compounds wherein Q is hydrogen and ---Z is —C can be obtained as described below in schema A.i (compound III-H).

Method B

The compounds B1, i.e compounds having formula (I) wherein ---Z represents =C can be obtained according to the method indicated in the following scheme A.i:

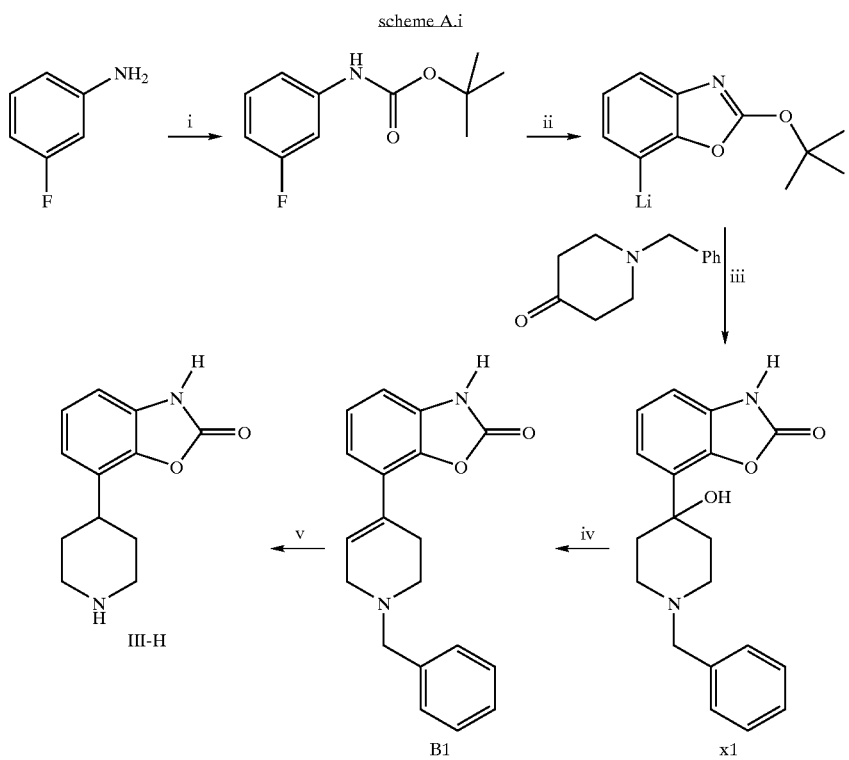

The starting compound for step (ii) can be obtained according to the procedure described in J. Org. Chem. 45, (1980), 4789, and step (ii) itself can be carried out as described in J. Org. Chem., 47, (1982), 2804.

Step (iii) is carried out in a manner known for this type of chemical reactions.

The Invention will be illustrated in the following Examples:

EXAMPLE 1

General Procedure for Method A:

a) To 1 mmol of halide Q-Hal, 0.8 mmol of I-H (---Z=— N) dissolved in 7.5 ml of $CH_3CN$ was added. Subsequently 0.43 ml (2.5 mmol) of (i-Pr)$_2$NEt was added and the resulting mixture was stirred for 3 hrs at 85° C. After the reaction mixture had reached roomtemperature, 7.5 ml of dichloromethane were added, the resulting solution was put on top of a solid phase extraction column (Varian 5 g type Si) and the fraction containing the desired product was subsequently put on top of a solid phase extraction column (Varian 5 g 0.8 meq./g type Strong Cationic Exchange (SCX), conditioned on MeOH, then $CH_2Cl_2$)) after which the column was washed 2 times with MeOH. Then, the latter column, was washed with 0.1 M $NH_3$/MeOH and eluton was performed with 1.0 M $NH_3$/MeOH. The eluate was concentrated in vacuo removing solvent and the rest of (i-Pr)$_2$NEt, yielding the expected product.

It is also possible to perform the purification with standard chromatographic procedures. In a single case (i.e. A1), the solvent used was dimethylformamide (DMF), see below.

b) 10.2 g (40 mmol) of I-H.HCl were suspended in 150 ml of DMF, to the stirred resulting mixture 21 ml (120 mmol) of (i-Pr)$_2$NEt were added. During a period of 10 minutes a solution of 7.0 g (41 mmol) of benzylbromide in 25 ml of DMF was added at room temperature, the process is, slightly exothermic (5–10° C.). Stirring was continued 3 hrs at room temperature after which the reaction mixture was poured on to 700 ml of water. Subsequently extraction was performed with 3×250 ml of ethylacetate, the combined organic fractions washed with 2×150 ml of water and dried with $MgSO_4$. Removal of the drying agent by filtration and of the solvent in vacuo yielded 10.5 g of raw product. The latter was purified by flash column chromatography ($SiO_2$, eluent $CH_2Cl_2$/MeOH 98/2), yielding 8.5 g (69%) of pure product A1 as a free base, m.p.: 189–190° C.

The compounds A2 to A46 as indicated in table A have been prepared analogously to procedure a) of method A.

TABLE A

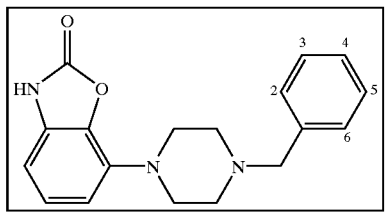

| compound | Hal | salt | melting point ° C. | position(s) substitution(s) | | | | |
|---|---|---|---|---|---|---|---|---|
| | | | | 2 | 3 | 4 | 5 | 6 |
| A1 | Br | fb | 189–90 | | | | | |
| A2 | Br | fb | 220–22 d | Br | | | | |
| A3 | Br | fb | 170–2 d | F | F | F | F | F |
| A4 | Br | fb | 220–2 d | | | CN | | |
| A5 | Br | fb | 130–2 d | | | OMe | | |
| A6 | Br | fb | 223–5 d | | | $SO_2Me$ | | |
| A7 | Br | fb | 235–7 d | Cl | | | | Cl |
| A8 | Br | fb | 190–2 d | F | | Me | | |
| A9 | Br | fb | 200–2 d | F | F | | | |
| A10 | Br | fb | 122–4 d | | | $SCF_3$ | | |
| A11 | Br | fb | >250 d | Cl | | | | Cl |
| A12 | Br | fb | 160–70 d | Me | | | | |
| A13 | Cl | fb | 165–7 d | | | OMe | | |
| A14 | Br | fb | 177–9 | | F | F | | |
| A15 | Br | fb | 150–2 | | | $OCF_3$ | | |
| A16 | Br | fb | 146–8 | | | Br | | |
| A17 | Br | fb | 193–5 | | Br | OMe | | |
| A18 | Br | fb | 170–1 | | F | F | F | |
| A19 | Br | fb | 195–7 | F | | | F | |
| A20 | Br | fb | 171–3 | $OCF_3$ | | | | |
| A21 | Br | fb | 191–6 d | | | Cl | Cl | |
| A22 | Br | fb | 183–6 | | | Me | | |
| A23 | Br | fb | 132–4 | | | $CF_3$ | | |
| A24 | Br | fb | 194–206 d | F | | F | | |
| A25 | Br | fb | 124–7 | $CF_3$ | | | | |
| A26 | Br | fb | 184–6 | | | tBut | | |
| A27 | Br | fb | 216–8 d | Cl | | | | |
| A28 | Br | fb | 115–20 | | $CF_3$ | F | | |
| A29 | Br | fb | 175–8 | $CF_3$ | | | | |
| A30 | Br | fb | 186–8 | Cl | | | $CF_3$ | |
| A31 | Br | fb | 197–200 | F | | F | | F |
| A32 | Br | fb | 159–63 | | | | Br | |
| A33 | Cl | fb | 152–8 d | | | Me | Me | |
| A34 | Br | fb | 178–83 | F | | | | |
| A35 | Br | fb | 215–9 | CN | | | | |
| A36 | Br | fb | 198–200 | | | Me | | Me |
| A37 | Br | fb | 190–5 | | | | Me | |
| A38 | Br | fb | 166–76 | | CN | | | |
| A39 | Br | fb | 188–90 | $CF_3$ | | F | | |
| A40 | Br | fb | 210–4 | Cl | | F | | |
| A41 | Br | fb | 180–6 | | | F | | |
| A42 | Br | fb | 159–63 | F | | | | |
| A43 | Br | fb | 178–80 | F | Cl | | | |

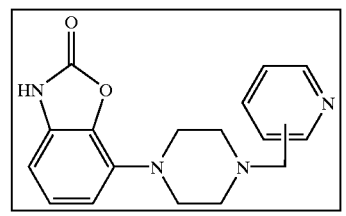

| compound | Hal | salt | melting point ° C. | Q |
|---|---|---|---|---|
| A44 | Cl | fb | 188–90 d | 2-pyridylmethyl |
| A45 | Cl | fb | 175–9 | 3-pyridylmethyl |
| A46 | Cl | fb | 230–5 d | 4-pyridylmethyl | d = decomposition
fb = free base

EXAMPLE 2

Step ii and iii (Scheme A.i):

Under an inert atmosphere, 16.5 g (78.2 mmol) of N-(tert.butyloxycarbonyl)-meta-fluoroaniline were dissolved in 230 ml of dry tetrahydrofuran (THF) after which the solution was cooled to −75° C. (dry ice, acetone). While stirring, a solution of tert.butyl-lithium in heptane (ca. 156 mmol, 2 molequivalents) was added slowly after which the reaction mixture was stirred for 0.5 hrs at −70° C., and subsequently for an additional 2 hrs at −25° C. Again the reaction mixture was brought to −75° C. and a solution of 14.4 ml N-benzylpiperidone (78 mmol, 1 molequivalent) in 25 ml of dry THF. The reaction mixture was allowed to reach room temperature and stirred for an additional 16 hrs. Subsequently, 250 ml of 2M HCl was carefully added, the resulting mixture was extracted with EtOAc (3×). The water layer was, while stirring, poured on to 84 g of $NaHCO_3$ after which the waterlayer was again extracted with EtOAc. The resulting organic layer was dried on $Na_2SO_4$. After removal of the drying agent by filtration and of the solvent by evaporation in vacuo, 15 g of a dark yellow oil was isolated. Column chromatography ($SiO_2$, eluent: $CH_2Cl_2$/MeOH 9/1) yielded 7.5 g (ca. 30%) of a light yellow foam. While stirring, 1 g of the foam was triturated with di-ethyl ether and a small volume of EtOAc. After 50 hrs the solid material was filtered and washed with with di-ethyl ether/hexane to yield 0.5 g of a nearly white solid ×1, mp 125–8° C.

Step iv (Scheme A.i):

While stirring, 6.3 g (19.4 mmol) of ×1 (scheme A.i.) was dissolved in 250 ml of dioxane after which 150 ml of concentrated HCl was added, the resulting mixture was refluxed for 1.5 hrs. The reaction mixture was allowed to reach room temperature after which it was poured on to 140 g of NaHCO₃, subsequently about 250 ml of EtOAc were added and an amount of water enough to solve all of the solid material, the pH was >7. The layers were separated and the waterlayer was extracted with EtOAc (2×). The combined organic fractions (3), were dried on Na₂SO₄. After removal of the drying agent by filtration and of the solvent by concentration in vacuo, 8 g of a dark yellow oil was isolated which solidified on standing. Column chromatography (SiO₂, eluent: EtOAc) yielded 4.56 g (ca. 30%) of a nearly white product. The latter was suspended in hexane and stirred for 20 hrs. Filtration and drying of the residue yielded 3.5 g (59%) of a white solid B1 as a free base, mp ca. 153° C.

EXAMPLE 3

Preparation of Intermediate III-H of Scheme A.i.
Step v (Scheme Ai):
2.71 g (8.9 mmol) of B1 of scheme A.i. were dissolved in 250 ml of absolute EtOH. To the latter solution 0.6 g of 20% Pd(OH)₂ on carbon was added after which the reaction mixture was subjected to hydrogenation for 18 hrs at roomtemperature. Subsequently the reaction mixture was filtered (hyflo supercel) and the residu (hyflo) washed with methanol/triethylamine 97/3. The filtrate was concentrated in vacuo yielding 1.87 g of a nearly white solid which was suspended in EtOAc and stirred for 20 hrs. Filtration of the solid and subsequently drying afforded 1.56 g (81%) of the intermediate III-H (scheme A.i.).

What is claimed is:
1. A compound having formula (I)

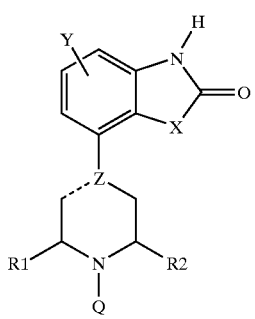

(I)

wherein
Y is hydrogen, halogen, alkyl (1–3C), CN, CF₃, OCF₃, SCF3, alkoxy(1–3C), amino or mono- or dialkyl(1–3C) substituted amino or hydroxy,
X is O or SO or SO₂,
---Z represents —C, =C or —N,
R₁ and R₂ independently represent hydrogen or alkyl (1–3C),
Q is a benzyl group or a 2-, 3- or 4-pyridylmethyl group, which groups may be substituted with one or more substituents, which are alike or different, chosen from halogen, nitro, cyano, amino, mono- and di (1–3C) alkylamino, (1–3C) alkoxy, CE₃, OCF₃, SCF₃, (1–4C)-alkyl, (1–3C)alkylsulfonyl and hydroxy, or a salt thereof.

2. The compound as claimed in claim 1, wherein Y, R₁ and R₂ are hydrogen, X represents oxygen, and Q is substituted or unsubstituted benzyl.

3. The compound as claimed in claim 2, wherein Q is unsubstituted benzyl and ---Z represents —N.

4. A method for the preparation of a compound as claimed in claim 1, comprising:
reacting a compound having the formula:

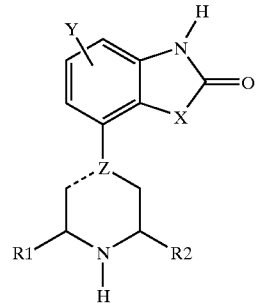

wherein X, Y, ---Z, R1 and R2 have the meanings given in claim 1 for a compound having formula (I),
with a compound of the formula Q-Hal wherein Q has the meaning given in claim 1 for a compound having formula (I) and Hal is halogen,
to yield a compound having formula (I).

5. A composition comprising at least one compound as claimed in claim 1, and at least one auxiliary substance.

6. A method of treating at least one CNS disorder in a human or animal patient in need of such treating, comprising administering to the patient at least one compound as claimed in claim 1 in an amount effective for the treating,
wherein the at least one CNS disorder is chosen from anxiety disorders, generalized anxiety, panic, obsessive compulsive disorder, depression, schizophrenia, Parkinson's disease, and combinations thereof.

7. A method of treating anxiety, depression, or a combination of anxiety and depression, in a human or animal patient in need of such treating, comprising administering to the patient at least one compound as claimed in claim 1 in an amount effective for the treating.

8. A method of treating Parkinson's Disease, in a human or animal patient in need of such treating, comprising administering to the patient at least one compound as claimed in claim 1 in an amount effective for the treating.

9. A method of treating schizophrenia, in a human or animal patient in need of such treating, comprising administering to the patient at least one compound as claimed in claim 1 in an amount effective for the treating.

10. A composition comprising at least one compound as claimed in claim 3, and at least one auxiliary substance.

* * * * *

UNITED STATES PATENT AND TRADEMARK OFFICE
CERTIFICATE OF CORRECTION

PATENT NO.    : 6,911,448 B2
DATED         : June 28, 2005
INVENTOR(S)   : Roelof W. Feenstra et al.

It is certified that error appears in the above-identified patent and that said Letters Patent is hereby corrected as shown below:

Title page,
Item [57], ABSTRACT,
Line 7, "wich" should read -- which --;
Line 8, "substited" should read -- substituted --; and Column 7,
Line 49, "SCF3," should read -- $SCF_3$, --.

Column 8,
Line 1, "$CE_3$," should read -- $CF_3$, --.

Signed and Sealed this

Twentieth Day of September, 2005

JON W. DUDAS
*Director of the United States Patent and Trademark Office*